US009494506B2

(12) United States Patent
Dyche et al.

(10) Patent No.: US 9,494,506 B2
(45) Date of Patent: Nov. 15, 2016

(54) APPARATUS FOR USE WITH A NEBULIZER AND A METHOD OF OPERATING A NEBULIZER

(71) Applicant: KONINKLIJKE PHILIPS N.V., Eindhoven (NL)

(72) Inventors: Anthony Dyche, Hayling Island (GB); Timothy Spencer, Chichester (GB); Charles David Hillier, Chichester (GB); Michael James Robbert Leppard, Hunston (GB)

(73) Assignee: Koninklijke Philips N.V., Eindhoven (NL)

( * ) Notice: Subject to any disclaimer, the term of this patent is extended or adjusted under 35 U.S.C. 154(b) by 276 days.

(21) Appl. No.: 14/380,103

(22) PCT Filed: Mar. 5, 2013

(86) PCT No.: PCT/IB2013/051734
§ 371 (c)(1),
(2) Date: Aug. 21, 2014

(87) PCT Pub. No.: WO2013/132427
PCT Pub. Date: Sep. 12, 2013

(65) Prior Publication Data
US 2015/0034076 A1    Feb. 5, 2015

Related U.S. Application Data

(60) Provisional application No. 61/607,638, filed on Mar. 7, 2012.

(51) Int. Cl.
*G01N 11/02*    (2006.01)
*G01F 3/00*    (2006.01)
(Continued)

(52) U.S. Cl.
CPC ............ *G01N 11/02* (2013.01); *A61M 11/005* (2013.01); *A61M 15/0085* (2013.01);
(Continued)

(58) Field of Classification Search
CPC ..... G01N 11/02; G01F 3/00; B05B 17/0615; B05B 12/02; B05B 12/004; B05B 7/0012; B05B 12/12; A61M 15/0085; A61M 11/005; A61M 2205/0294; A61M 2205/3327; A61M 2205/3379; A61M 2205/52; A61M 2205/60
USPC ................ 604/207, 30–34, 65–67; 73/54.13, 73/54.17, 61.77, 64.52, 1.31; 702/45; 128/200.16, 200.23, 200.18
See application file for complete search history.

(56) References Cited

U.S. PATENT DOCUMENTS 5,363,842 A    11/1994 Mishelevich et al.
6,237,589 B1    5/2001 Denyer et al.
(Continued)

FOREIGN PATENT DOCUMENTS

EP    1465692 A1    2/2010
WO    03061741 A1    7/2003
(Continued)

*Primary Examiner* — Tan-Uyen (Jackie) T Ho
*Assistant Examiner* — Mark Wardas

(57) ABSTRACT

There is provided a method of determining whether a first type of liquid is being used in a nebulizer, the method comprising obtaining a measurement of the time taken by the nebulizer to nebulize a specified volume of liquid that was held therein, comparing the time taken to nebulize the specified volume of liquid to an estimated value for the time required to nebulize the same volume of the first type of liquid, and determining whether the liquid nebulized by the nebulizer was the first type of liquid based on the comparison.

13 Claims, 3 Drawing Sheets

(51) Int. Cl.
*A61M 11/00* (2006.01)
*A61M 15/00* (2006.01)
*B05B 12/00* (2006.01)
*B05B 12/02* (2006.01)
*B05B 17/06* (2006.01)
*A61M 16/00* (2006.01)
*B05B 7/00* (2006.01)
*B05B 12/12* (2006.01)

(52) U.S. Cl.
CPC ............ *B05B 12/004* (2013.01); *B05B 12/02* (2013.01); *B05B 17/0615* (2013.01); *G01F 3/00* (2013.01); *A61M 2016/0024* (2013.01); *A61M 2016/0036* (2013.01); *A61M 2205/0294* (2013.01); *A61M 2205/3327* (2013.01); *A61M 2205/3334* (2013.01); *A61M 2205/3379* (2013.01); *A61M 2205/50* (2013.01); *A61M 2205/52* (2013.01); *A61M 2205/587* (2013.01); *A61M 2205/6009* (2013.01); *A61M 2205/6018* (2013.01); *A61M 2205/6054* (2013.01); *A61M 2205/70* (2013.01); *B05B 7/0012* (2013.01); *B05B 12/12* (2013.01)

(56) References Cited

U.S. PATENT DOCUMENTS

| | | | |
|---|---|---|---|
| 7,451,760 | B2 | 11/2008 | Denyer et al. |
| 2007/0074722 | A1 | 4/2007 | Giroux et al. |
| 2010/0280486 | A1* | 11/2010 | Khair ............... A61M 5/142 604/506 |

FOREIGN PATENT DOCUMENTS

| | | |
|---|---|---|
| WO | 2009013504 A2 | 1/2009 |
| WO | 2011021118 A1 | 2/2011 |

* cited by examiner

```
┌─────────────────────────────────────────────┐
│ Determine the type of liquid to be used in  │──101
│ the nebuliser and the volume to be nebulised│
└─────────────────────────────────────────────┘
                      ↓
┌─────────────────────────────────────────────┐
│  Determine/estimate the time required to    │──103
│  nebulise the required volume of that liquid│
└─────────────────────────────────────────────┘
                      ↓
┌─────────────────────────────────────────────┐
│           Operate the nebuliser to          │──105
│          nebulise liquid held therein       │
└─────────────────────────────────────────────┘

┌─────────────────────────────────────────────┐
│   Measure the time required for the nebuliser│──107
│    to nebulise the required volume of liquid │
└─────────────────────────────────────────────┘
                      ↓
┌─────────────────────────────────────────────┐
│          Compare the measured time to       │──109
│          the determined/estimated time      │
└─────────────────────────────────────────────┘
                      ↓
┌─────────────────────────────────────────────┐
│  Determine whether the liquid nebulised     │──111
│  by the nebuliser was the type determined   │
│  in step 101 based on the comparison        │
└─────────────────────────────────────────────┘
```

FIG. 2

| Drug type | Colistin 2 sec inhalation | | Salbutamol 2 sec inhalation | | D-nase 2 sec inhalation | |
|---|---|---|---|---|---|---|
| | AT (sec) | TT (sec) | AT (sec) | TT (sec) | AT (sec) | TT (sec) |
| | 73 | 316 | 45 | 201 | 32 | 145 |
| | 59 | 260 | 39 | 174 | 34 | 157 |
| | 58 | 252 | 42 | 186 | 38 | 170 |
| | 61 | 265 | 41 | 182 | 41 | 183 |
| | 48 | 211 | 42 | 183 | 44 | 195 |
| | 51 | 221 | 41 | 179 | 40 | 179 |
| | 57 | 250 | 40 | 176 | 43 | 188 |
| | 64 | 278 | 41 | 180 | 39 | 171 |
| | 58 | 255 | 43 | 187 | 39 | 174 |
| | 60 | 263 | 42 | 184 | 22 | 105 |
| | 49 | 213 | 43 | 193 | 43 | 191 |
| | 60 | 261 | 55 | 239 | 40 | 179 |
| | 57 | 249 | 44 | 198 | 40 | 180 |
| | 44 | 210 | 43 | 189 | 45 | 200 |
| | 57 | 246 | 45 | 198 | 40 | 175 |
| | 53 | 229 | 45 | 197 | 43 | 192 |
| | 52 | 230 | 50 | 218 | 45 | 196 |
| | 60 | 263 | 40 | 181 | 46 | 201 |
| | 51 | 222 | 43 | 190 | 46 | 205 |
| | 57 | 251 | 41 | 185 | 37 | 167 |
| | 56 | 243 | 39 | 181 | 40 | 180 |
| Mean | 56 | 247 | 43 | 191 | 40 | 178 |
| STDEV | 6 | 25 | 4 | 15 | 5 | 22 |

FIG. 3

APPARATUS FOR USE WITH A NEBULIZER AND A METHOD OF OPERATING A NEBULIZER

CROSS-REFERENCE TO PRIOR APPLICATIONS

This application is the U.S. National Phase application under 35 U.S.C. §371 of International Application No. PCT/IB2013/051734, filed on Mar. 5, 2013, which claims the benefit of U.S. Provisional Patent Application No. 61/607,638, filed on Mar. 7, 2012. These applications are hereby incorporated by reference herein.

TECHNICAL FIELD OF THE INVENTION

The invention relates to a nebulizer that nebulizes a liquid held therein into fine droplets, for example for inhalation by a user, and in particular relates to determining whether the liquid nebulized by the nebulizer is the correct or appropriate type of liquid.

BACKGROUND TO THE INVENTION

Nebulizers, or atomizers as they are sometimes called, are devices that generate a fine spray or aerosol from a liquid. A particularly useful application for nebulizers is to provide a fine spray containing a dissolved or a suspended particulate drug for administration to a patient by inhalation.

Piezo-mesh based nebulizers are commonly used to generate aerosols in such drug delivery apparatus, whereby for instance a piezoelectric element vibrates a nozzle plate (also referred to as a mesh) to produce the fine aerosol spray. In some nebulizers the piezoelectric element is bonded to, or otherwise in contact with, a nozzle plate element, whereas in other nebulizers the nozzle plate element is separate from (i.e. not in contact with) the piezoelectric element.

The rate at which the liquid is atomized is affected by the operation and design of the nebulizer and also by the properties of the liquid. In some types of nebulizers (for example pneumatic jet-type nebulizers), the rate can be known for a particular combination of nebulizer and medication, and it is possible to estimate a dosage of medication delivered to a patient based on the total time that the aerosol is generated and inhaled by the patient.

However, in nebulizers that use a mesh to nebulize the liquid, the rate or amount of droplets produced varies over time as the holes in the mesh become blocked. This means that it is not possible to calculate the dosage delivered to the patient in the same way as for pneumatic jet-type nebulizers. Instead, in piezo-mesh nebulizers a volumetric metering method may be used to make sure that the correct dose is provided to the patient. In particular, prior to use with a particular medication, the nebulizer is fitted with a metering chamber that holds only the required volume of medication for a single dose. Such volumetric metering methods are described in EP 1465692.

Medication for use in nebulizers may be supplied in a range of containers or vials and are typically supplied to the patient in quantities sufficient for treatment over a number of days (e.g. 30). The amount of medication to be delivered during each use of the nebulizer (dosage) can be set by making use of a data carrier that is associated with the medication container or vial and that contains specific treatment information that is read by the nebulizer prior to use. The data carrier can also be used to store details of each completed dose or treatment (e.g. the proportion of the dose delivered to the patient and the type of medication administered).

This data can subsequently be uploaded to a computer for analysis using suitable software, and this allows a healthcare professional to monitor that the patient is correctly using the device and undergoing the prescribed treatment.

Typically, prior to use of the nebulizer, a patient is required to fit an appropriately sized metering chamber into the nebulizer and pour the required medication from a vial into the metering chamber. Once the medication has been poured in, the nebulizer can read the data carrier associated with the medication (and also any data carrier associated with the metering chamber) and set its operating parameters accordingly.

However, a single nebulizer can be used with a range of different liquid medications, and patients are often prescribed more than one type of drug at a time. Although the use of a data carrier on the metering chamber allows the fitting of the correct metering chamber to be determined, and the nebulizer can read the data carrier associated with the medication packaging, there is currently no way of verifying that the correct medication has been poured into the nebulizer.

The loading of the wrong medication into the nebulizer can cause a number of problems. In particular, some protein drugs, such as Dinase and A1 AT, can be damaged if they are contaminated with other drug substances, but more importantly, if the wrong medication is loaded into a metering chamber that is for use with another medication, the wrong dosage (or even an inappropriate liquid) could be administered to the patient. For example, colistimethate sodium may have an inhaled dose size of 0.3 ml and hypertonic saline may have an inhaled dose size of 1.0 ml—and therefore mixing up the medications will result in the wrong dosage being given to the patient when the nebulizer is used).

Therefore, there is a need for a technique to check or verify that the correct liquid (medication) has been dispensed by a nebulizer.

SUMMARY OF THE INVENTION

According to a first aspect of the invention, there is provided a method of determining whether a first type of liquid is being used in a nebulizer, the method comprising (i) obtaining a measurement of the time taken by the nebulizer to nebulize a specified volume of liquid that was held therein; (ii) comparing the time taken to nebulize the specified volume of liquid to an estimated value for the time required to nebulize the same volume of the first type of liquid; and (iii) determining whether the liquid nebulized by the nebulizer was the first type of liquid based on the comparison.

In step (iii), it may be determined that the liquid nebulized by the nebulizer was the first type of liquid if the time taken to nebulize the specified volume of liquid is within a predetermined amount of the estimated value for the time required to nebulize the same volume of the first type of liquid.

The method may further comprise, prior to step (i), the steps of: determining the identity of the first type of liquid to be nebulized by the nebulizer; determining the volume of the first type of liquid to be nebulized by the nebulizer, the volume being the specified volume; and estimating the time required to nebulize the specified volume of the first type of liquid.

The step of determining the identity of the first type of liquid and/or the determining the volume of the first type of liquid may comprise reading a data carrier associated with a container for the first type of liquid and/or a metering chamber in the nebulizer or by reading a memory of the nebulizer.

The method may further comprise the step of: determining the rate at which the first type of liquid should be nebulized by the nebulizer; wherein the step of estimating the time required to nebulize the specified volume of the first type of liquid makes use of the determined rate and the determined volume.

The time taken by the nebulizer to nebulize the specified volume of liquid may be the total time from the start of the operation of the nebulizer to the point when the last of the specified volume of liquid was nebulized.

Alternatively, the time taken by the nebulizer to nebulize the specified volume of liquid may be the total time from the start of the operation of the nebulizer to the point when the last of the specified volume of liquid was nebulized, excluding the time when a user of the nebulizer is exhaling.

The method may further comprise, prior to step (i), the steps of: operating the nebulizer to nebulize the specified volume of liquid held therein; and measuring the time taken to nebulize the specified volume of liquid.

The method may further comprise: repeating step (i) and averaging the obtained measurements of the time taken; and step (ii) may comprise comparing the average time taken to nebulize the specified volume of liquid to the estimated value for the time required to nebulize the same volume of the first type of liquid.

According to another aspect of the invention, there is provided a computer program product comprising computer readable code embodied therein, the computer readable code being configured such that, upon execution by a suitable computer or processor, the computer or processor performs the method described above.

According to another aspect of the invention, there is provided an apparatus that comprises a processor that is configured to obtain a measurement of the time taken by a nebulizer to nebulize a specified volume of liquid that was held therein; compare the time taken to nebulize the specified volume of liquid to a predetermined value for the time required to nebulize the same volume of a first type of liquid; and determine whether the liquid nebulized by the nebulizer was the first type of liquid based on the comparison.

The processor can be configured to determine that the liquid nebulized by the nebulizer was the first type of liquid if the time taken to nebulize the specified volume of liquid is within a predetermined amount of the estimated value for the time required to nebulize the same volume of the first type of liquid.

The processor can be further configured to determine the identity of the first type of liquid to be nebulized by the nebulizer; determine the volume of the first type of liquid to be nebulized by the nebulizer, the volume being the specified volume; and estimate the time required to nebulize the specified volume of the first type of liquid.

In some embodiments, the apparatus can be part of a control unit of a nebulizer. In alternative embodiments, the apparatus can be separate from the nebulizer, for example in the form of a computer or other electronic device, and can obtain the measurement of the time taken by the nebulizer to nebulize a specified volume of liquid that was held therein through any suitable wired or wireless communication link with the nebulizer.

According to another aspect of the invention, there is provided a nebulizer that comprises a chamber for holding liquid to be nebulized; a nebulizing element; an actuator that is configured to vibrate the nebulizing element or liquid held in the chamber to nebulize the liquid held in the chamber; and a control unit as described above.

BRIEF DESCRIPTION OF THE DRAWINGS

Exemplary embodiments of the invention will now be described, by way of example only, with reference to the following drawings, in which:

FIG. 2 is a flow chart illustrating a method of operating a nebulizer according to an embodiment of the invention; and FIG. 3 shows some experimental results illustrating the differences in performance of a nebulizer for three different liquids.

Figure 1:
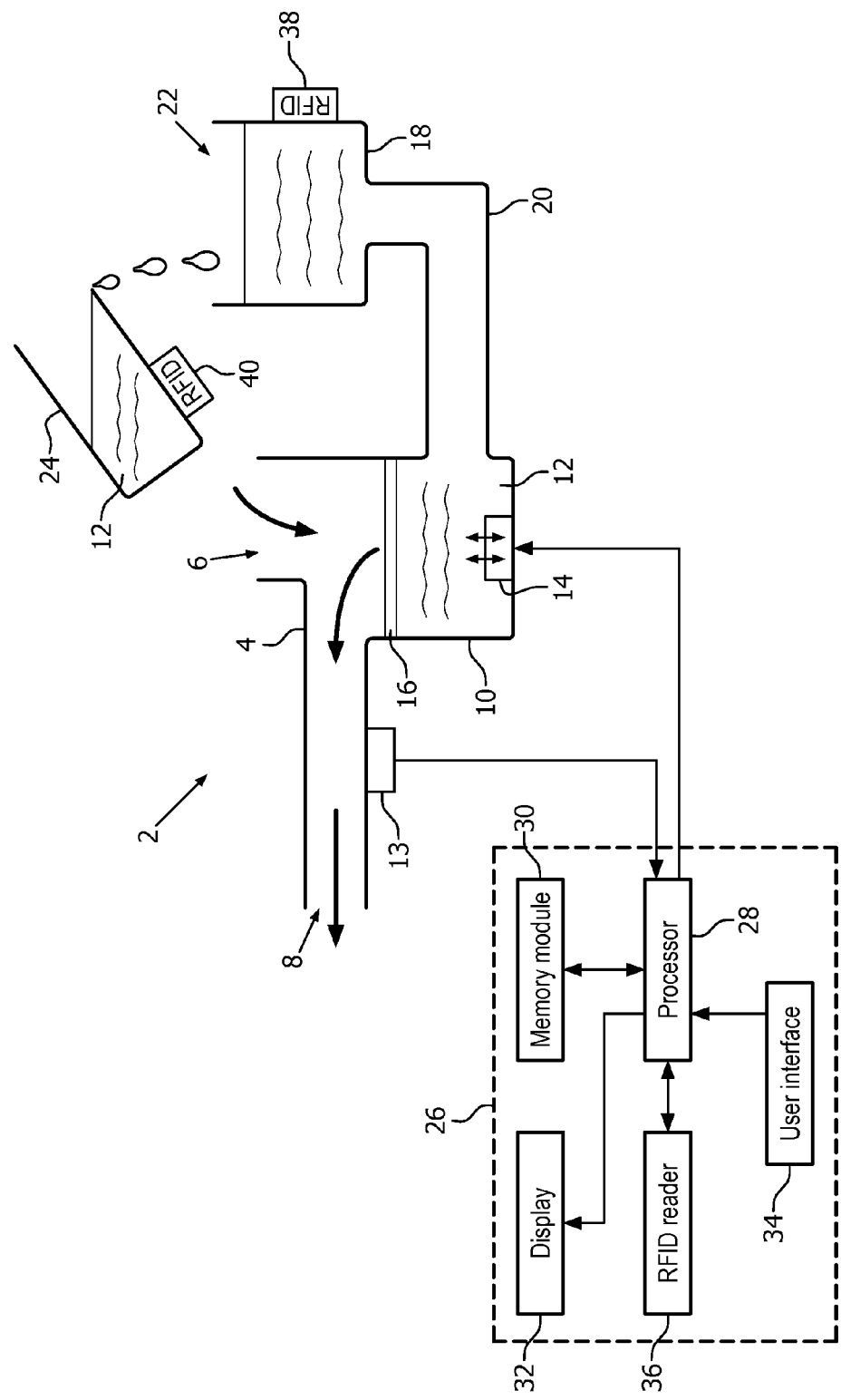
FIG. 1 is a block diagram of a nebulizer according to an embodiment of the invention.

DETAILED DESCRIPTION OF THE PREFERRED EMBODIMENTS

FIG. 1 shows an exemplary nebulizer 2. The nebulizer 2 comprises a body or housing 4 having an inlet 6 and an outlet 8 arranged so that when a user of the nebulizer 2 inhales through the outlet 8, air is drawn into and through the nebulizer 2 via the inlet 6 and outlet 8 and into the user's body. The outlet 8 is typically provided in the form of a mouthpiece or a facial or nasal mask or in a form that is suitable for connection to a separate replaceable mouthpiece or facial or nasal mask. The housing 4, inlet 6 and outlet 8 are also arranged so that the user can exhale through the nebulizer 2.

The nebulizer 2 comprises a nebulizing chamber 10 located between the inlet 6 and outlet 8 that holds a liquid 12, for example a medication or drug, that is to be nebulized (i.e. to be turned into a fine mist or spray). The nebulizer 2 is configured such that fine droplets of the nebulized liquid 12 combine with the air drawn through the nebulizer 2 when the user inhales to deliver a dose of the medication or drug to the user.

An air flow sensor 13 is arranged in the nebulizer 2 that detects the direction in which air is flowing through the housing 4. This information can be used to determine when the user is inhaling and exhaling.

An actuator 14 is provided for agitating or vibrating the liquid 12 held in the nebulizing chamber 10. In the embodiments of the invention that are described further below, the actuator 14 is provided in the form of a piezoelectric element. However, those skilled in the art of nebulizers will appreciate that other forms of actuator 14 can be used in nebulizers according to the invention. It will also be appreciated that a piezoelectric element 14 can be covered with a plastic or metal cover layer to avoid direct contact between the piezoelectric element and the liquid 12 (although alternative types of material can be used for the cover layer).

A nozzle plate 16 is provided in the nebulizing chamber 10 for nebulizing the liquid 12 when the liquid 12 is vibrated by the actuator 14. The nozzle plate 16 is typically in the form of a mesh or membrane having a plurality of small holes or nozzles through which small amounts of the liquid can pass. The size (diameter) of the nozzles in the nozzle plate 16 determines, among other things, the size of the droplets of liquid produced when the nebulizer 2 is activated. In some embodiments, the nozzle plate 16 is removable from the nebulizer 2 so that it can be cleaned or completely replaced, as required.

In the illustrated embodiment, the actuator 14 is separate from the nozzle plate 16 and is positioned at, or proximate to, the bottom of the nebulizing chamber 10 in order to agitate the liquid 12. However, in alternative embodiments the actuator 14 can be in contact with or integral with the nozzle plate 16 and can vibrate the nozzle plate 16 in order to nebulize the liquid 12.

In use, the liquid 12 fills the nebulizing chamber 10 up to the height of the nozzle plate 16. It will be appreciated that the liquid 12 in the nebulizing chamber 10 will be depleted as the nebulizer 2 is operated, and more liquid 12 must be added to the reservoir chamber 10 to maintain the liquid 12 at the required height for the nebulizer 2 to continue operating. Therefore, the nebulizer 2 comprises a metering chamber 18 that stores liquid for replenishing the liquid 12 in the nebulizing chamber 10. The liquid from the metering chamber 18 may flow into the nebulizing chamber 10 through a connecting tube 20 due to the action of gravity and/or capillary filling.

The metering chamber 18, in combination with the nebulizing chamber 10 (and connecting tube 20), holds the total volume of liquid 12 that is to be nebulized during a single use of the nebulizer 2.

In the case where the liquid is a medication, as the volume of the liquid 12 to be nebulized will depend on the prescribed course of treatment, the nebulizer 2 can be configured so that it is possible to remove the metering chamber 18 from the nebulizer 2 and replace it with another metering chamber having a different size, thereby changing the total volume of liquid 12 that can be held by the nebulizer 2. However, in some embodiments, the metering chamber may be integral with the rest of the nebulizer 2 and cannot be removed. In that case, the metering chamber 18 may include some visual marking or other indication of the volumes of liquid 12 that can be held by the chamber 18 so that the user can determine whether they have poured in the appropriate amount of liquid 12 into the chamber 18. In some embodiments, the metering chamber 18 comprises a metering chamber and an overflow chamber separated by a barrier such as that described in EP 1465692.

The metering chamber 18 has a closable opening 22 into which the user can pour in the liquid to be nebulized from a liquid container (or vial) 24 prior to commencing operation of the nebulizer 2.

The nebulizer 2 further comprises a control unit 26 that controls the operation of the nebulizer 2. The control unit 26 comprises a processor 28 that is electrically connected to the air flow sensor 13 and the actuator 14. When the processor 28 determines from the information received from the air flow sensor 13 that the user is inhaling, the processor 28 outputs control signals to the actuator 14 to cause the actuator 14 to operate (vibrate) and thereby nebulize the liquid 12. When the processor 28 determines from the information received from the air flow sensor 13 that the user has stopped inhaling, the processor 28 ceases the operation (vibration) of the actuator 14.

In one embodiment, the control signals output to the actuator 14 by the processor 28 cause the actuator 14 to operate in a 'pulsed' operation mode. In this mode, the control signal causes the actuator 14 to actuate at a frequency f for a particular number of cycles in a row, and then causes the actuator 14 to rest for a further number of cycles. This actuated and non-actuated operation is repeated during the operation of the nebulizer 2.

A memory module 30 is also provided in the control unit 26 that can store operating parameters and/or program instructions for use by the processor 28 during operation of the nebulizer 2. The operating parameters may, for example, relate to the treatment regimen to be provided by the nebulizer 2, such as the required treatment time, required treatment volume (dosage) and/or medication flow rate. As described further below, the memory module 30 can also store information relating to the time required to deliver particular volumes of specific liquids (or the time required to deliver a unit volume of a particular liquid), and information on the previous use of the nebulizer 2 by the user (for example the time taken to deliver a particular dose of liquid, the metering chamber 18 used, the medication dispensed, etc.).

The control unit 26 further comprises a display 32 that is for displaying information on the status of the nebulizer 2 to the user. The display may comprise an LCD screen or other suitable type of display, or can comprise one or more LEDs or lights. The display 32 can present information indicating, for example, whether the nebulizer 2 is ready for use and the dosage time and/or amount remaining.

The control unit 26 further comprises a user interface 34 for allowing the user to operate the nebulizer 2. The user interface can comprise a single button, switch or other input means that can be used for powering on or otherwise activating the nebulizer 2, or multiple input means that allow the user to select various settings or options for the nebulizer 2.

In the illustrated embodiment, the control unit 26 further comprises a radio-frequency identification (RFID) tag reader 36 that is used for reading information stored on an RFID tag 38 that is associated with (e.g. attached to) the metering chamber 18 (in embodiments where different metering chambers 18 can be used in the nebulizer 2), and an RFID tag 40 that is associated with the liquid 12 to be nebulized (for example the RFID tag 40 could be attached or otherwise associated with the packaging of the liquid 12—liquid container 24, or the RFID tag may be supplied separately to the liquid container 24). The RFID tag reader 36 can read the information on RFID tags 38, 40 and pass it to the processor 28 for further processing. The processor 28 can use this information to configure the nebulizer 2 for operation and to verify that an appropriate combination of liquid 12 and metering chamber 18 is being used in the nebulizer 2.

The information stored in the RFID tag 38 that is attached to the metering chamber 18 can indicate the volume of the metering chamber 18 and/or the specific medication that the metering chamber 18 is to be used with. The indication of the volume of the metering chamber 18 can be provided as an actual volume, or alternatively the RFID tag 38 can store an ID number for the metering chamber 18 which the processor 28 can use to query information on various types of metering chambers 18 stored in the memory module 30.

The information stored in the RFID tag 40 that is attached to the liquid container 24 can include the identity of the liquid that the container 24 holds and the dosage regime to be provided by the nebulizer 2 (i.e. the volume to be dispensed each time that the nebulizer 2 is used, how often the volume is to be dispensed, and/or how quickly the volume is to be dispensed).

It will be appreciated that it is possible in some embodiments for only the liquid container 24 to have an RFID tag associated therewith, with the metering chamber 18 merely being provided with some visual indication (e.g. color coding) for the user to check that they are using the correct chamber 18 in the nebulizer 2.

Those skilled in the art will be aware of alternative types of data carriers and their respective wired or wireless readers that can be used in nebulizer 2. For example, the metering chamber 18 can be provided with electrical contacts that allow the metering chamber 18 to be electrically connected to the control unit 26 when the metering chamber 18 is installed in the nebulizer 2. This way the processor 28 can directly interrogate an electronic component in or on the metering chamber 18 for the information stored therein, and it also provides a way for the processor 28 to verify that the metering chamber 18 has been correctly fitted in the nebulizer 2.

As suggested above, nebulizer 2 can be supplied to a particular user and then used with any suitable medication prescribed by the user's healthcare professional, and it is possible the user may be prescribed more than one type of medication to use at different times in the nebulizer 2 to treat a particular medical condition. As described above, the nebulizer 2 can determine the treatment regimen (i.e. the particular liquid 12 to be nebulized and the required dosage) and can determine or assume that an appropriate metering chamber 18 is used for that liquid 12 (in the embodiments where the metering chamber 18 is interchangeable).

As described below, the invention provides a way of verifying or checking that the liquid 12 nebulized by the nebulizer 2 was the right liquid 12 (e.g. the liquid 12 that was specified by the treatment regimen).

In particular, it has been found that different types of liquid are nebulized at different rates (depending on the particular characteristics of the liquid 12), and it is therefore possible to determine whether the correct liquid was nebulized by comparing an estimate of the time required to nebulize the required volume of the correct liquid to the actual time taken to nebulize the required volume of the liquid 12 that was in the nebulizer 2. If the time taken differs from the estimated time by more than a predetermined amount, then it can be assumed that the wrong liquid 12 was nebulized by the nebulizer 2. In some embodiments, the comparison can be made using an average of the time taken to nebulize the required volume liquid 12 over a number of cycles of operation.

The invention is applicable to any type of nebulizer 2 in which the volume to be dispensed in a particular operation cycle is known or otherwise controlled, and in which the rate at which the liquid 12 is nebulized depends, at least in part, on the characteristics of the liquid 12, such as viscosity, surface tension, temperature and whether the liquid is a solution or suspension. The rate at which the liquid 12 is nebulized is also affected by the type (design) of the nebulizer 2.

A flow chart illustrating a method of operating the nebulizer 2 in accordance with a specific embodiment of the invention is shown in FIG. 2.

In step 101, the type of liquid 12 that it is intended to use in the nebulizer 2 is determined, along with the volume to be nebulized during a single cycle of operation. As described above, this information can be obtained by reading information stored in an RFID tag 40 associated with a liquid container 24 using RFID reader 36. This information can be read at, or around, the time that the user is pouring the liquid into the metering chamber 18.

In addition, or alternatively, this information can be stored in the memory module 30, in which case the processor 28 can read the information from the memory module 30 and verify the information with that retrieved from the RFID tag 40. This step can also comprise reading an RFID tag 38 associated with the metering chamber 18 installed in the nebulizer 2, and comparing the volume of the installed metering chamber 18 to the volume to be nebulized during the single cycle of operation. In the event of a mismatch (i.e. the metering chamber 18 does not provide the right volume for the specified liquid 12), the control unit 26 can indicate an error to the user using the display 32.

In step 103, the time or average time required to nebulize the specified volume of liquid 12 is estimated. This estimation can be made by using information on the time required to nebulize a unit volume of the liquid 12 (or alternatively the actual volume to be nebulized) that is stored in the memory module 30 and/or in the RFID tag 40 associated with the liquid container 240. Preferably, the time required to nebulize the specified volume of liquid corresponds to the time required for the actuator 14 to be active to nebulize the liquid 12, and it does not include the time when the actuator 14 is inactive during a cycle of operation (i.e. where the user is exhaling). Alternatively, however, the time required can also take into account the time the user spends exhaling; although it will be appreciated that this requires information on the typical breathing pattern of the user to be stored in the memory module 30 of the control unit 26). The output rate for a nebulizer 2 may vary with the particular characteristics and current state of the nozzle plate 16, the first of which may be determined by calibrating the nozzle plate 16 during manufacture and storing the output rate for that nozzle plate 16 on an additional tag on the nozzle plate assembly, and the second of which can be determined by evaluating the time taken to nebulize the specified volume of liquid 12 over a number of different treatment cycles.

In step 105, operation of the nebulizer 2 to nebulize the specified volume of liquid 12 that is held in the nebulizing chamber 10 and metering chamber 18 is started. As described above, when the processor 28 determines from the information received from the air flow sensor 13 that the user is inhaling, the processor 28 outputs control signals to the actuator 14 to cause the actuator 14 to nebulize the liquid 12 held in the nebulizing chamber 10. When the processor 28 determines from the information received from the air flow sensor 13 that the user has stopped inhaling, the processor 28 ceases the operation of the actuator 14. When the next inhalation is sensed, the processor 28 again activates the actuator 14. This process continues until all of the liquid 12 held in the nebulizing chamber 10 and metering chamber 18 has been nebulized. The processor 28 may determine when this has happened by monitoring for a change in the electrical impedance of the drive signal of the actuator 14 that occurs when the nebulizing chamber 10 runs dry.

While the nebulizer 2 is operating, the processor 28 records the time that the actuator 14 is active during inhalations from the start of the first inhalation to the point where the last of the specified volume of liquid 12 has been nebulized (i.e. excluding the times when the user is exhaling and the actuator 14 is inactive). This is shown as step 107 in FIG. 2. Optionally, the processor 28 can also record the total time required to nebulize the specified volume of liquid 12, i.e. the total time from the start of the first inhalation to the end of the final inhalation when all of the liquid 12 has been nebulized, which includes the times when the user is exhaling.

Once the operation of the nebulizer 2 has been completed (i.e. the specified volume of liquid 12 has been nebulized), the measurement of the time taken to nebulize the liquid 12 during the operation of the nebulizer 2 is compared to the time estimated in step 103 (step 109).

This comparison allows the determination of whether the liquid 12 actually nebulized by the nebulizer 2 was the liquid determined in step 101 (step 111). In particular, if the measurement of the time taken differs from the estimated time by less than a predetermined threshold, it can be determined that the liquid 12 nebulized by the nebulizer 2 was the expected liquid. However, if the measurement of the time taken differs from the estimated time by more than the predetermined amount, it can be determined that the liquid 12 nebulized by the nebulizer 2 was not the expected liquid.

In this case, the nebulizer 2 can optionally provide an indication on the display 32 to prompt the user to check the liquid and specified volume when pouring the liquid into the nebulizer 2 the next time the nebulizer 2 is to be used. In addition, or alternatively, the control unit 26 can provide a message to the healthcare professional of the user indicating that they may have used the wrong liquid 12 in the nebulizer 2.

The threshold may be set based on the particular type of drugs being monitored, taking into account the difference in the mean treatment time for different drugs. For example, the mean treatment time for a specific drug may be significantly different to the mean treatment time for another drug commonly prescribed in conjunction with the specific drug and the threshold could be set accordingly. This would be the case in distinguishing between colistin and D-nase for example, which have been found to have mean treatment times of 56 and 40 seconds respectively for a particular nebulizer configuration, as shown in FIG. 3, which is discussed further below. In some cases, the difference between the mean treatment times is less significant and the threshold could be set accordingly. For example, as shown in FIG. 3, the mean treatment times of salbutamol and D-nase are 43 and 40 seconds respectively.

However, as there will be some variation in treatment times for a particular liquid 12, it is preferable to monitor a number of treatment cycles to determine the average time required to nebulize the required volume of liquid 12 and therefore to determine if the correct liquid 12 is being used. Therefore, in some embodiments of the invention, steps 101 to 107 are performed for a number of cycles for a particular liquid and volume to be nebulized and the average of the measurement times determined. In this case, the average is compared to the estimated time and a determination made as to whether the correct liquid has been nebulized (step 109 and 111).

Some experimental results illustrating the differences in performance of a nebulizer 2 (in which the actuator 14 directly vibrates the nozzle plate 16) for different liquids are shown in FIG. 3. In particular, the performance of a nebulizer was evaluated over 21 cycles for each of three different medications, colistin, salbutamol and D-nase. In each case, 0.3 ml of liquid was nebulized. The table in FIG. 3 shows how long the actuator 14 was active during each cycle (denoted the actuating time—AT) and the total time taken from the start to the end of each cycle (total time—TT). The mean for each of the AT and TT are provided, along with the standard deviation.

By deeming differences to be significant at, for example, a 95% level of confidence ($p<0.05$), the results in FIG. 3 show that the difference between the mean ATs for colistin and salbutamol, colistin and D-nase and salbutamol and D-nase are significant, and therefore the method set out in FIG. 2 will be able to provide a reliable indicator of whether a user of the nebulizer 2 has used the correct liquid 12.

It will be appreciated by those skilled in the art that all of the steps in the method of FIG. 2 can be performed in the nebulizer 2, but alternatively only some of the steps can be performed by the control unit 26, with the remaining steps being performed by a general purpose computer, smart phone or server. In particular alternative implementations, the processor 28 in the nebulizer 2 may perform steps 101, 105 and 107 and supply the information and time measurements to another electronic device, such as a general purpose computer, smart phone or server, through a wired or wireless connection (including through the Internet), and that device can perform the operations described in steps 103, 109 and 111. This electronic device may be associated with the healthcare professional of the user, which allows the healthcare professional to be presented with messages and information on the use of the nebulizer 2 by the user.

It will also be appreciated that, in addition to the control unit 26 and processor 28 described above, the invention can be provided in the form of a computer program carried on a computer readable medium (for example memory module 30) that is configured to cause the processor 28 in the control unit 26 to execute some or all of the steps shown in FIG. 2. A computer program can also or alternatively be provided that is configured to cause a computer, smart phone or other suitable type of electronic device to obtain the time measurement recorded by the nebulizer 2 in step 107 and to perform the method in steps 109 and 111 to determine if the correct liquid was present in the nebulizer 2.

Those skilled in the art will appreciate that the word "nebulizer" can be used interchangeably with the term drug delivery apparatus or atomizer, and the use of the word "nebulizer" is intended to cover forms and designs of nebulizer other than the specific type of nebulizer described above and illustrated in the Figures.

Furthermore, although the invention has been described in terms of a nebulizer that is primarily for use in administering a medication, it will be appreciated that the invention can be applied to nebulizers or devices in which a liquid is nebulized for other purposes, such as, for example an air humidifier, an electric shaver, a steam iron or a perfume dispenser.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining whether a first type of liquid is being used in a nebulizer, the method comprising:

(i) obtaining a measurement of the time taken by the nebulizer to nebulize a specified volume of liquid that was held therein;

(ii) comparing the time taken to nebulize the specified volume of liquid to an estimated value for the time required to nebulize the same volume of the first type of liquid; and (iii) determining whether the liquid nebulized by the nebulizer was the first type of liquid based on the comparison.

2. A method as claimed in claim 1, wherein, in step (iii) it is determined that the liquid nebulized by the nebulizer was the first type of liquid if the time taken to nebulize the specified volume of liquid is within a predetermined amount of the estimated value for the time required to nebulize the same volume of the first type of liquid.

3. A method as claimed in claim 1, the method further comprising, prior to step (i), the steps of:
determining the identity of the first type of liquid to be nebulized by the nebulizer;

determining the volume of the first type of liquid to be nebulized by the nebulizer, the volume being the specified volume; and estimating the time required to nebulize the specified volume of the first type of liquid.

4. A method as claimed in claim 3, wherein the step of determining the identity of the first type of liquid and/or the determining the specified volume of the first type of liquid comprises reading a data carrier associated with a container for the first type of liquid and/or a metering chamber in the nebulizer or by reading a memory of the nebulizer.

5. A method as claimed in claim 3, further comprising the step of:
determining the rate at which the first type of liquid should be nebulized by the nebulizer;
wherein the step of estimating the time required to nebulize the specified volume of the first type of liquid makes use of the determined rate and the determined volume.

6. A method as claimed in claim 1, wherein the time taken by the nebulizer to nebulize the specified volume of liquid is the total time from the start of the operation of the nebulizer to the point when the last of the specified volume of liquid was nebulized.

7. A method as claimed in claim 1, wherein the time taken by the nebulizer to nebulize the specified volume of liquid is the total time from the start of the operation of the nebulizer to the point when the last of the specified volume of liquid was nebulized, excluding the time when a user of the nebulizer is exhaling.

8. A method as claimed in claim 1, the method further comprising, prior to step (i), the steps of:

operating the nebulizer to nebulize the specified volume of liquid held therein; and measuring the time taken to nebulize the specified volume of liquid.

9. A method as claimed in claim 1, further comprising:

repeating step (i) and averaging the obtained measurements of the time taken; and wherein step (ii) comprises comparing the average time taken to nebulize the specified volume of liquid to the estimated value for the time required to nebulize the same volume of the first type of liquid.

10. An apparatus, comprising:

a processor that is configured:

to obtain a measurement of the time taken by a nebulizer to nebulize a specified volume of liquid that was held therein;

to compare the time taken to nebulize the specified volume of liquid to a predetermined value for the time required to nebulize the same volume of a first type of liquid; and to determine whether the liquid nebulized by the nebulizer was the first type of liquid based on the comparison.

11. An apparatus as claimed in claim 10, wherein the processor is configured to determine that the liquid nebulized by the nebulizer was the first type of liquid if the time taken to nebulize the specified volume of liquid is within a predetermined amount of the estimated value for the time required to nebulize the same volume of the first type of liquid.

12. An apparatus as claimed in claim 10, wherein the processor is further configured to determine the identity of the first type of liquid to be nebulized by the nebulizer; determine the volume of the first type of liquid to be nebulized by the nebulizer, the volume being the specified volume; and estimate the time required to nebulize the specified volume of the first type of liquid.

13. A nebulizer, comprising:

a chamber for holding a liquid to be nebulized;

a nebulizing element;

an actuator that is configured to vibrate the nebulizing element or liquid held in the chamber to nebulize the liquid held in the chamber; and a control unit comprising an apparatus as claimed in claim 10.

* * * * *